US005188099A

United States Patent [19]

Todeschini et al.

[11] Patent Number: 5,188,099

[45] Date of Patent: Feb. 23, 1993

[54] THERAPEUTIC EXERCISE CHAMBER WITH CONTROLLED OZONATED ENVIRONMENT

[76] Inventors: Carlo Todeschini, Via per Maggiana, 11 - 22054 Mandello Del Lario - Como; Gabriella Togni, Via C. Battisti, 11 - 22066 Mariano Comense - Como, both of Italy

[21] Appl. No.: 537,960

[22] Filed: Jun. 13, 1990

[30] Foreign Application Priority Data

Jun. 13, 1989 [IT] Italy ........ 20857 A/89

[51] Int. Cl.[5] ........ A62B 31/00; A61M 15/02; A61G 10/00; A61H 33/14

[52] U.S. Cl. ........ 128/205.26; 128/202.25; 128/202.12

[58] Field of Search ........ 128/202.25, 202.26, 128/202.12, 202.13, 200.24, 204.18, 205.11, 205.26, 369, 370, 371, 372, 373, 374

[56] References Cited

U.S. PATENT DOCUMENTS

| | | | |
|---|---|---|---|
| 365,067 | 6/1887 | Harris | 128/202.12 |
| 476,548 | 7/1892 | Nixon | 128/202.12 |
| 826,029 | 7/1906 | Harper | 128/202.12 |
| 904,172 | 11/1908 | Batter | 128/202.12 |
| 1,336,774 | 4/1920 | Cooper | 128/374 X |
| 1,773,220 | 8/1930 | Credicott | 128/202.25 |
| 2,700,384 | 1/1955 | Nory | 128/205.24 X |
| 2,756,754 | 7/1956 | Poffenbarger | 128/373 |
| 2,920,622 | 1/1960 | Steel | 128/202.25 |
| 3,311,108 | 3/1967 | Cristofv | 128/202.25 |
| 4,509,513 | 4/1985 | Lasley | 128/202.12 |
| 4,582,055 | 4/1986 | McDougal et al. | 128/202.12 |
| 4,884,574 | 12/1989 | Hardie | 128/373 |
| 4,893,615 | 1/1990 | Khabirova | 128/24.2 |

FOREIGN PATENT DOCUMENTS

| | | | |
|---|---|---|---|
| 1454567 | 1/1969 | Fed. Rep. of Germany | 128/202.25 |
| 1808201 | 5/1970 | Fed. Rep. of Germany . | |
| 2303970 | 2/1974 | Fed. Rep. of Germany . | |
| 1204523 | 8/1959 | France | 128/373 |
| 2102886 | 4/1972 | France . | |
| 482683 | 12/1951 | Italy | 128/202.25 |
| 524914 | 4/1955 | Italy | 128/202.25 |
| 580023 | 7/1958 | Italy | 128/373 |
| 342389 | 7/1978 | U.S.S.R. | 128/205.26 |
| 895442 | 1/1982 | U.S.S.R. | 128/205.26 |
| 5375 | of 1913 | United Kingdom | 128/202.25 |
| 2219203 | 6/1989 | United Kingdom . | |

*Primary Examiner*—Edgar S. Burr
*Assistant Examiner*—E. P. Raciti
*Attorney, Agent, or Firm*—Sughrue, Mion, Zinn, Macpeak & Seas

[57] ABSTRACT

An apparatus for practicing gymnastics, which imparts to a user an enhanced slimming effect with special regard to reducing cellulitis, comprises a base on which a gymnastic implement is arranged, a rigid hood mounted on the base, a means of delivering an ozonized flow of heated air under the hood, and a humidifier device.

3 Claims, 3 Drawing Sheets

THERAPEUTIC EXERCISE CHAMBER WITH CONTROLLED OZONATED ENVIRONMENT

BACKGROUND OF THE INVENTION

This invention relates to an apparatus for practicing gymnastics under a controlled atmosphere, being of a type which comprises a base, a hood associated with the base, having an opening of a selected size, and defining an enclosure in cooperation with the base, a gymnastic implement placed within said enclosure, and a delivery means of delivering a heated air flow into said enclosure.

As is known, growing acceptance is met at gymnasia and aesthetic centers for the care of the body by apparatus of the kind specified above, which enable the beneficial effects of gymnastics to be combined with those to be derived from application of heat.

The problem that underlies this invention is to provide an apparatus as above which has such construction and performance characteristics as to provide improved slimming effect especially as regards reduction of cellulitis.

SUMMARY OF THE INVENTION

This problem is solved according to the invention by an apparatus as indicated being characterized in that the delivery means comprises an ozonizer device active on the heated air flow entering said enclosure.

Advantageously, according to a preferred aspect of the invention, the apparatus further comprises a device for introducing steam into the enclosure.

The features and advantages of an apparatus according to the invention will become apparent from the following detailed description of a preferred embodiment thereof, given by way of illustration and not of limitation with reference to the accompanying drawings.

DETAILED DESCRIPTION OF THE INVENTION

Figure 1:
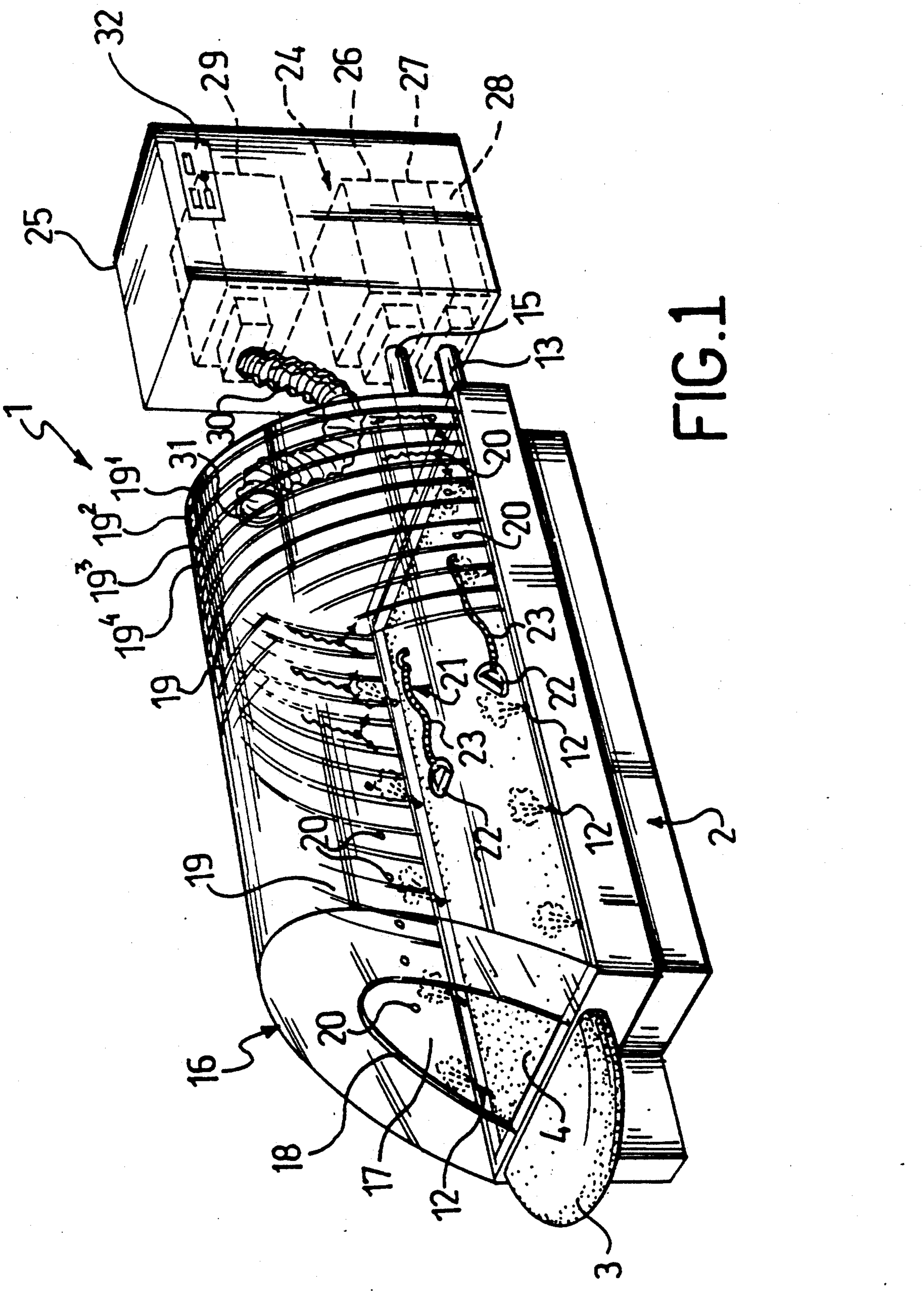
FIG. 1 is a perspective view showing schematically an apparatus according to the invention.
Figure 2:
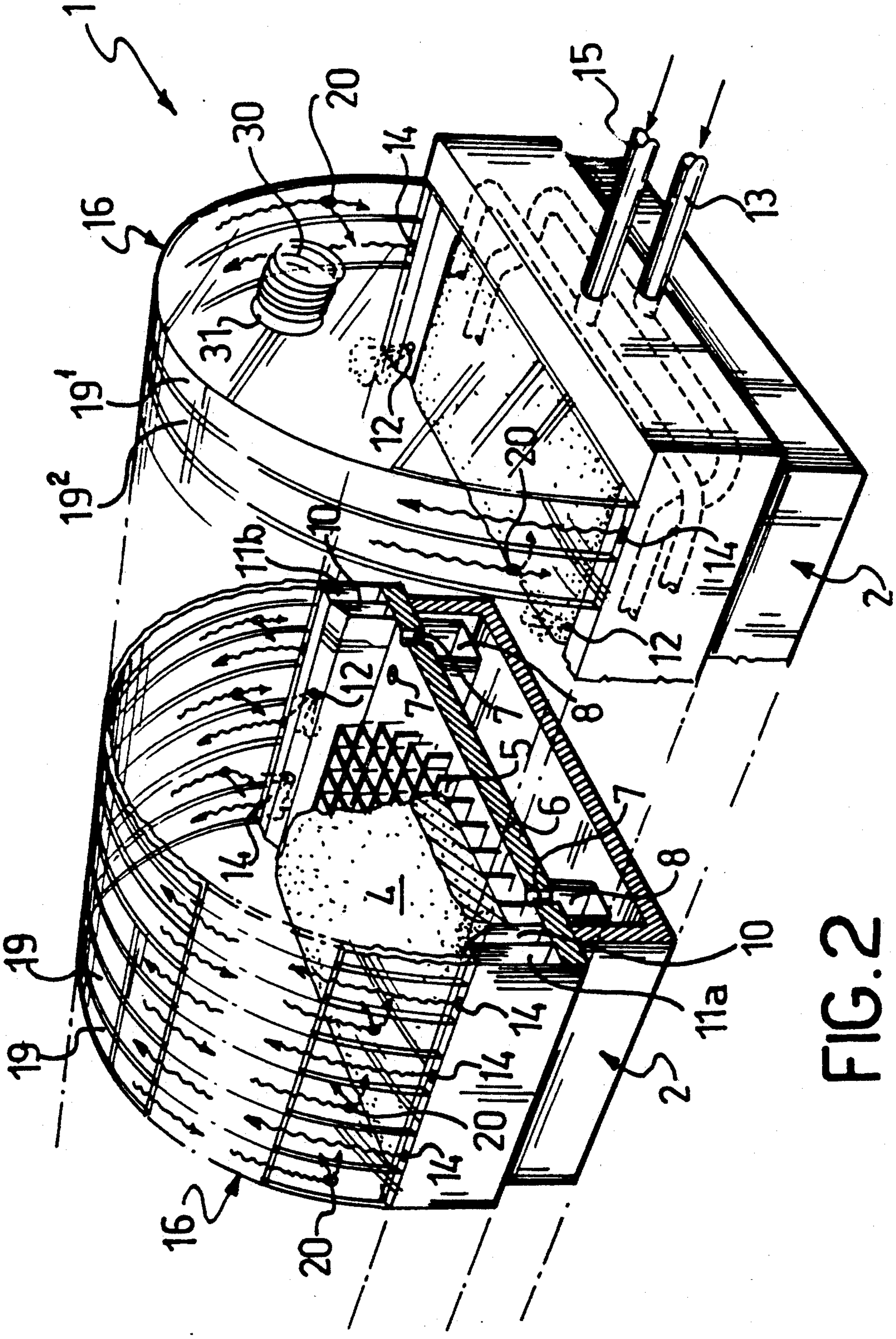
FIG. 2 is a part-sectional perspective view showing schematically a detail of the apparatus in FIG. 1.
Figure 4:
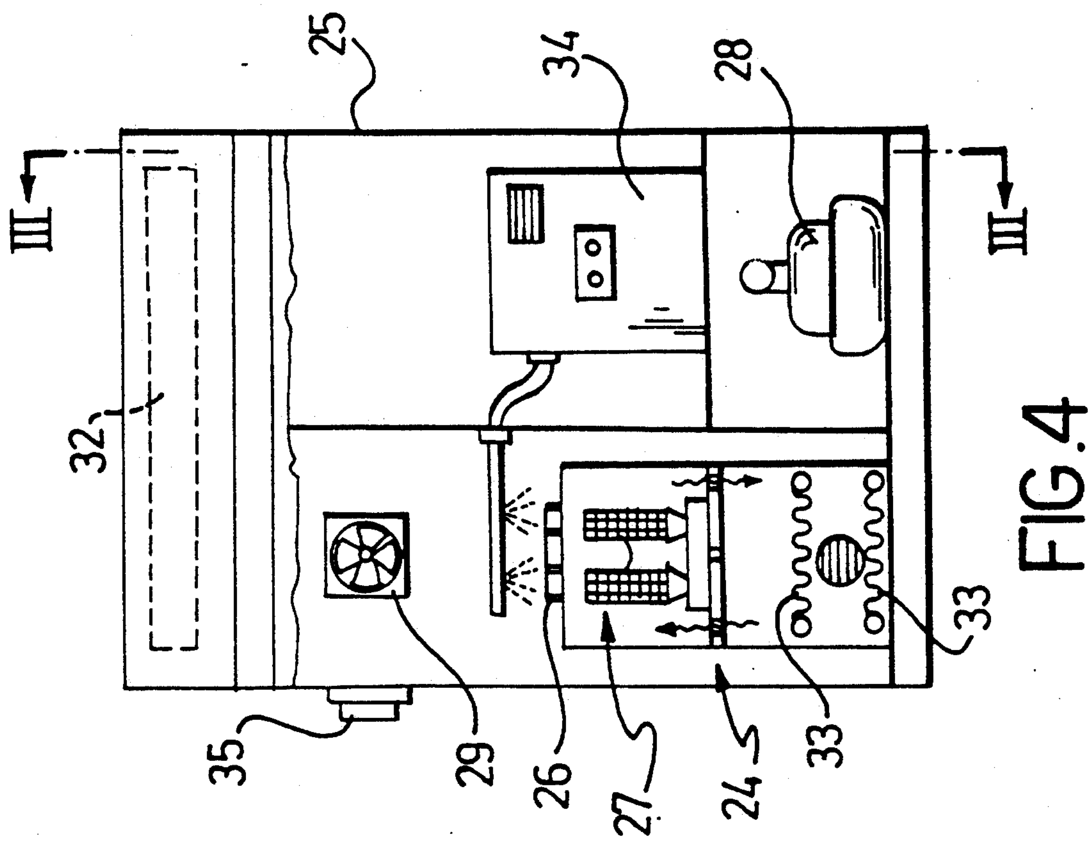
FIG. 4 is a detail transverse view of the apparatus in FIG. 1, taken on the line IV—IV.
Figure 3:
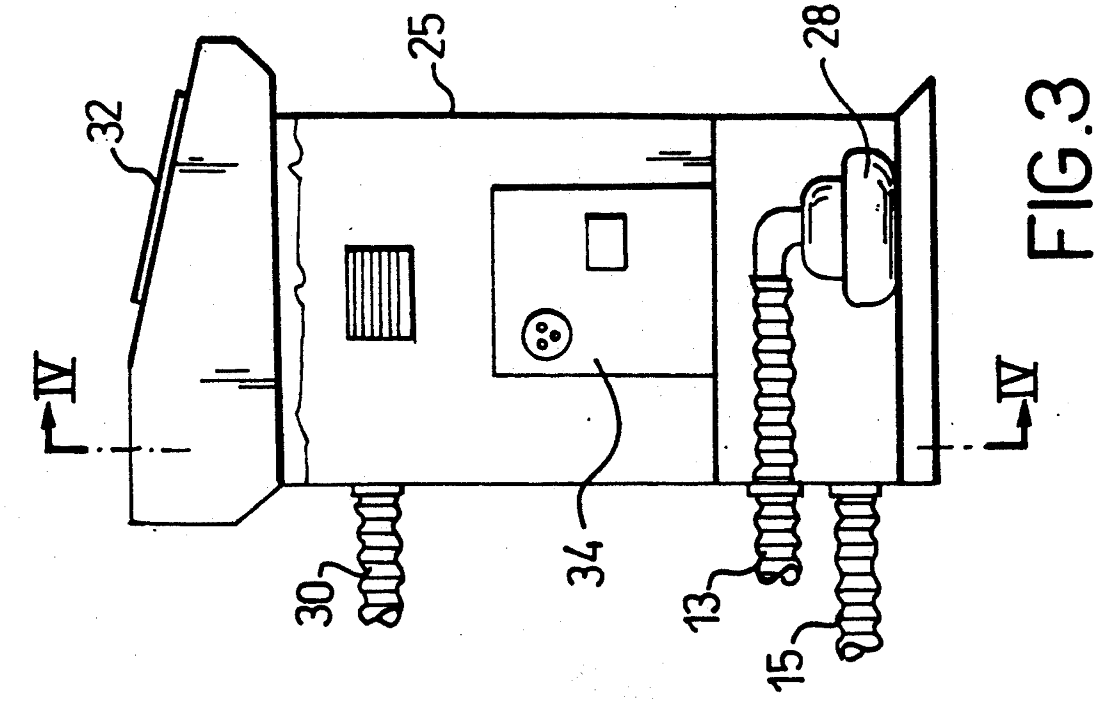
FIG. 3 is a detail side view of the apparatus in FIG. 1, taken on the line III—III.

With reference to the drawing views, generally shown at 1 is an apparatus according to the invention for practicing gymnastics under a controlled atmosphere.

The apparatus 1 comprises a base 2 with a substantially parallelepiped shape and provided with a headrest 3.

The base 2 is provided upwardly with a mat 4 resting on a plastics grille 5 mounted in the base 2 on a deck 6 made of a suitable plastics such as Formica. The deck 6 beneath the grille 5 is formed with a plurality of through holes 7 which open into two condensation water collecting pans, both indicated at 8 and arranged in the base 2.

Formed in the deck 6 along each major side of the mat 4 are two conduits, respectively an inner one 10 and outer one 11*a*or 11*b*, lying adjacent but separate from each other. Specifically, an inner conduit 10 and outer conduit 11*a* are provided on one side while an inner conduit 10 and an outer conduit 11*b* are provided on the opposite side. The two inner conduits 10, lying next to the mat 4, are provided with a plurality of steam delivery nozzles, as explained hereinafter, and in communication with a header 13 mounted in the base 2 at the location of a minor side thereof remote from the headrest 3.

The two outer conduits 11*a*, 11*b* are provided upwardly with a plurality of openings 14 lined up in each conduit at pitch distances apart; the outer conduits 11*a* , 11*b* are also connected to a respective header 15 provided in the vicinity of the header 13.

Mounted over the base 2 is a rigid semi-transparent hood 16, substantially semi-cylindrical in shape, which defines, in cooperation with the base 2, an enclosure 17 adapted to accommodate the body of the apparatus 1 user, lying down on the mat 4. At the location of the headrest 3, the hood 16 is formed with an opening 18 so sized as to allow the user's body to pass therethrough.

Advantageously, the hood 16 is formed from a plastics material, preferably a polycarbonate-based one, in the form of a void sheet wherein a plurality of parallel, adjacent and separate channels 19 are defined which extend circumferentially of the hood and are open at their opposite ends.

It is noted that such opposite ends of the channels 19 are located at the openings 14 in the two outer conduits 11*a* and 11*b*. In addition, for each outer conduit 11*a*, 11*b* there is provided one opening 14 between every two channels 19; in particular, in the outer conduit 11*a* on the one side there is provided a respective opening 14 every odd-numbered channel 19 (19$^1$, 19$^3$ . . . .), whereas in the outer conduit 11*b* on the opposite side, there is provided a respective opening 14 every even-numbered channel 19 (19$^2$, 19$^4$ . . . .).

Each channel 19 is formed, moreover, with a window 20 opening into the enclosure 17; in particular, in the odd-numbered channels 19, the windows 20 are located close to the outer conduit 11*b*, and conversely, the windows of the even-numbered channels 19 locate close to the outer conduit 11*a*.

Indicated at 21 is a gymnastic implement housed in the enclosure 17; in the example under consideration, the gymnastic implement 21 consists of a pair of handgrips 22 connected to the base 2 by respective elastic means 23.

The apparatus 1 comprises a delivery means, generally shown at 24, for delivering an air flow into the enclosure 17. Specifically, the means 24 comprises, housed within a parallelepiped structure 25 separated from the base 2, a fan 26, in this embodiment a 20-watt, 30-cubic meter per minute fan, the delivery end of which is connected to the header 15, and electric heater means comprising electric resistance heaters 33. In this embodiment, two 1200-watt resistance heaters are provided. Also provided is an ozonizer device 27 mounted at the location of the fan 26 for ozonizing the heated air flow entering the enclosure 17.

In this embodiment, the ozonizer device 27 comprises twelve ozonizing lamps with an ozone capacity of 20 mg/hour.

Upstream of the fan 26 and the ozonizer device 27, a conventional oxygen concentrator device is active, as shown at 34. In this embodiment, it is sized to deliver 4 liters per minute of oxygen-enriched air.

Indicated at 28 is a humidifier device housed in the structure 25 and connected to the header 13 for introducing steam into the enclosure 17 through the nozzles 12.

The structure 25 also includes a suction fan 29 having a duct 30 connected to an inlet fitting 31 formed on the hood 16 for drawing out air from the enclosure at the end of a treatment cycle and exhausting it through an outlet fitting 35.

On the parallelepiped structure 25 there is mounted a control panel 32 including gauges, switches, and the like means of measurement and control, among which a thermostat and a timer connected to the means 24 of delivering the ozonized heated air flow for the purpose of controlling and adjusting to selected values the air temperature, operation of the ozonizer device and proportion of ozone in the air, as well as the moisture level of the air within the enclosure 17 and the treatment cycle duration.

The operation of the apparatus 1 according to the invention will be described herein below.

With the user lying down on the mat 4 and his/her body inside the enclosure 17, and performing gymnastic exercises by means of the implement 21, the treatment begins with operation of the fan 26 and the ozonizer device 27 to admit a flow of ozonized heated air into the header 15, and thence through the outer conduits 11*a*, 11*b* and the channels 19 of the hood 16. This air flow reaches then the interior of the enclosure 17 via the windows 20. Simultaneously therewith, the humidifier device 28 is operated to generate a flow of steam flowing through the header 13, the inward conduits 10, and the nozzles 12 into the enclosure 17.

It is noted that any fogging of the hood 16 would be prevented by the heated air blows through the hood channels 19. In addition, by virtue of the regular layout of the windows 20, the ozonized flow of heated air is uniformly distributed throughout the enclosure 17.

Any condensation water formed would fall through the grille 5 underlying the mat 4 and the holes 7 formed in the deck 6 into the pans 9.

Thus, a controlled atmosphere of humid air is created within the enclosure 17 which has a predetermined proportion of ozone, preferably of approximately 0.2 $mg/m^3$ and is at a desired temperature (37° C. to 40° C.) for the set treatment time.

Advantageously, moreover, the values of temperature, proportion of ozone, and air humidity within the enclosure are read from the gauges on the control panel 32, thereby enabling assisting personnel to act as more appropriate to keep the values constant or change them, if required.

During the treatment, muscles reach a high temperature quite rapidly owing to the heated air; in this way, a peripheral vasodilatory effect is induced which enhances the transfer of oxygen from the capillary vessels to the muscle, so that the latter can be allowed to work at full efficiency at once.

Having thus pre-conditioned the muscle by appropriate heat application, this will be enabled to act without excessive wearing exactly in those areas where cellulit is located. At the same time, through the skin pores expanded by the heat and softened by the action of moisture, ozone will be circulated which attacks with its free oxygen atom the chains of the unsaturated fatty acids to shorten them and convert the fatty molecules from lipophilic to hydrophilic. Thus, the cellulitic tissue will be absorbed and eliminated.

Additionally the ozone will also provide a disinfecting, anti-fungus, anti-viral, anti-bacterial, and curative effect of various troubles affecting the blood vessels.

Furthermore, during the treatment, the controlled atmosphere as described will purify and invigorate the user's skin.

On completion of the treatment, the fan 26, ozonizer device 27, and humidifier device 28 are turned off and the suction fan 29 is turned on to exhaust the ozonized warm air and steam from the enclosure 17, before the user gets out through the opening 18 in the hood 16.

A major advantage of the inventive apparatus is that it has afforded an enhanced slimming effect with special regard to reducing cellulitis.

A further advantage of the apparatus of this invention is that it enables the muscle heating time to be shortened, being therefore conducive to savings of energy by the user during a stage of low effectiveness as concerns reduction of cellulitis, and consequently to an ability to spend it more effectively during the stage when the muscles have been heated.

For equal results, the added advantage is also afforded of having a treatment of shorter duration, and accordingly, of a more profitable utilization of the apparatus.

A further advantage is obtained by the user inasmuch as his/her skin is purified and invigorated during the treatment. In addition, he/she is made the subject of a disinfecting action.

Another advantage of the invention is that it provides for accurate control of the conditions of the atmosphere within which the individual is treated.

The apparatus described in the foregoing is obviously susceptible to many changes and modifications. As an example, the shapes and dimensions of the base and the hood may be changed, or the gymnastic implement housed within the enclosure may be modified , without departing from the true scope of this invention as set forth in the appended claims.

What is claimed is:

1. An apparatus for practicing gymnastics under a controlled atmosphere, comprising:

a base;

a hood provided over the base and having an opening of a selected size, and defining an enclosure in cooperation with the base;

a gymnastic device within said enclosure which is designed for allowing an individual to exercise while in said enclosure;

a delivery means for delivering heated air into said enclosure, said delivery means including an ozonizer device for ozonizing the heated air flow entering said enclosure; and a humidifier for introducing steam into said enclosure;

wherein said ozonizer device comprises a plurality of ozonizing lamps having an ozone capacity of 20 mg/hour and an oxygen concentrator is located upstream of the ozonizer device for supplying oxygen-enriched air to said enclosure.

2. An apparatus according to claim 1, further comprising a plurality of channels formed within the hood and communicating with said delivery means and enclosure, the ozonized heated air flowing therethrough.

3. An apparatus according to claim 2, wherein said hood comprises a plurality of conduits provided therein for supplying said air to said enclosure.

* * * * *